(12) United States Patent
Backer et al.

(10) Patent No.: US 7,960,419 B2
(45) Date of Patent: Jun. 14, 2011

(54) SUBSTITUTED CARBOXAMIDES

(75) Inventors: Ryan Thomas Backer, Minniapolis, MN (US); Matthew Joseph Fisher, Mooresville, IN (US); Sean Patrick Hollinshead, Indianapolis, IN (US); Steven Lee Kuklish, Fishers, IN (US); Edward C R Smith, Fishers, IN (US); Kumiko Takeuchi, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 361 days.

(21) Appl. No.: 12/300,415

(22) PCT Filed: Jun. 7, 2007

(86) PCT No.: PCT/US2007/070572
§ 371 (c)(1),
(2), (4) Date: Nov. 11, 2008

(87) PCT Pub. No.: WO2008/103185
PCT Pub. Date: Aug. 28, 2008

(65) Prior Publication Data
US 2009/0182025 A1    Jul. 16, 2009

Related U.S. Application Data

(60) Provisional application No. 60/811,839, filed on Jun. 8, 2006.

(51) Int. Cl.
A61K 31/425 (2006.01)
C07D 275/03 (2006.01)
A61P 25/04 (2006.01)

(52) U.S. Cl. .................................. 514/372; 548/214
(58) Field of Classification Search .................. 514/372; 548/214

See application file for complete search history.

(56) References Cited

U.S. PATENT DOCUMENTS 5,538,939 A    7/1996    Muenster et al.

FOREIGN PATENT DOCUMENTS

| EP | 0 129 407 A | 12/1984 |
| EP | 0 640 597 A | 3/1995 |
| WO | WO 95/12587 A | 5/1995 |
| WO | WO 2005/113534 A | 12/2005 |
| WO | WO 2006/033005 A | 3/2006 |

OTHER PUBLICATIONS

J. Goerdeler, H. W. Pohland, Chemische Berichte, vol. 94, 1961, pp. 2950-2959.
J. Goerdeler, H. W. Pohland, Angew. Chem., vol. 72, No. 2, 1960, p. 77.
Chem. Abstr. 56:38461 (1992).
Chem. Abstr. 56:25070 (1962).
Augelli-Szafran, C.E.; Schwarz, R.D., Annual Reports in 'Medicinal Chemistry (2003) 38, 21-30.

*Primary Examiner* — Sharmila G. Landau
*Assistant Examiner* — Kortney L Klinkel
(74) *Attorney, Agent, or Firm* — Nelsen L. Lentz; Thomas E. Jackson

(57) ABSTRACT

This application relates to a substituted carboxamide compound of formula I, or a pharmaceutically acceptable salt thereof, as defined herein, a pharmaceutical composition thereof, and its use in treating pain.

10 Claims, No Drawings

SUBSTITUTED CARBOXAMIDES

This application claims the benefit of U.S. Provisional Application No. 60/811,839, filed Jun. 8, 2006.

This invention relates to certain substituted carboxamides, particularly certain N-acylated substituted 5-amino-4-methylisothiazole derivatives, as well as to processes for their preparation, pharmaceutical compositions comprising the substituted carboxamides, and methods for their use.

L-Glutamate is the major excitatory neurotransmitter in the central nervous system and is referred to as an excitatory amino acid. Glutamate receptors are composed of two major subtypes: the ligand-gated ion-channel ionotropic receptors, and the G-protein-coupled seven-transmembrane-domain metabotropic receptors (mGluRs). The metabotropic family comprises eight members and is sub-divided into three groups based on sequence similarity, signal transduction, and pharmacology. Group I receptors (mGluR$_1$ and mGluR$_5$, and their splice variants) are positively coupled to inositol phosphate hydrolysis and the generation of an intracellular calcium signal. Group II receptors (mGluR$_2$ and mGluR$_3$) and Group III receptors (mGluR$_4$, mGluR$_6$, mGluR$_7$, and mGluR$_8$) are negatively coupled to adenylyl cyclase and regulate cyclic AMP levels by indirectly inhibiting adenylyl cyclase activity. Group I receptors are located primarily post-synaptically and increase neuronal excitation, whereas Group II and Group III receptors are located primarily presynaptically and function as autoreceptors to decrease the excessive release of glutamate. Thus, the mGlu receptor subtypes have unique expression patterns in the central nervous system, which can be targeted with new and selective agents. See, for example, Augelli-Szafran, C. E.; Schwarz, R. D. Annual Reports in Medicinal Chemistry (2003) 38, 21-30 in which mGluR$_1$ antagonists are described as useful as neuroprotective agents in animal models of cerebral infarction, in models of pain involving spinal nerve ligation, in a formalin-induced pain model and in a migraine model. Also, mGluR$_1$ antagonists have been shown to be useful in (seizure) models of epilepsy and in (anti)anxiety models. In tissues in which mGluR$_1$ receptors are found, they may be implicated in pain.

Glutamate is the major excitatory neurotransmitter conveying sensory information onto neurons in the spinal cord and CNS during persistent pain states. Clinical chronic or persistent pain is postulated to depend at least in part on long-term increases in synaptic efficacy of glutamatergic inputs to somatosensory neurons of the spinal cord and supraspinal nociceptive regions following intense peripheral stimuli, tissue injury or nerve damage. This enhanced synaptic transmission leads to a reduction in pain threshold, an amplification of pain responses and a spread of pain sensitivity to non-injured areas. Immunocytochemical data demonstrate that mGlu$_1$ receptors are expressed in several regions of the ascending glutamatergic nociceptive pathways. Evidence indicates that stimulation of mGlu$_1$ receptors promotes an increase in neuronal excitation and fast glutamateregic synaptic transmission. The long-lasting actions of the intracellular signal transduction mechanisms recruited by mGlu$_1$ receptor stimulation support these receptors for sustaining central sensitization both at the spinal cord level and at the supraspinal level. Thus, a reduction of excitation by an mGlu$_1$ receptor antagonist is expected to provide a useful therapy for treatment of persistent pain conditions.

Further support for the use of an mGlu$_1$ receptor antagonist to ameliorate nociceptive responses induced by chronic inflammatory and non-inflammatory nociceptive stimuli in behavioral studies has been reported: The selective mGlu$_1$ receptor antagonist LY456236 can reduce nocifensive responses in the formalin test and mechanical allodynia in the L5/L6 spinal nerve ligation model of neuorpathic pain. See, Varty, G. B., et al., Psychopharmacology (Berl.). (2005), 179, 207-217.

The compounds of the present invention are selective antagonists of the Group I metabotropic receptors, particularly the mGluR$_1$ receptor (mGluR$_1$), especially with respect to mGluR$_2$, mGluR$_3$ and mGluR$_4$; and they may be selective with respect to mGluR$_5$. As such they are useful for the treatment of conditions associated with those metabotropic glutamate receptors, such as pain, particularly chronic pain (or persistent pain), for example chronic neuropathic pain, chronic inflammatory/joint related pain, or chronic non-inflammatory/non-neuropathic pain (NINN pain), as well as for treatment of migraine or epilepsy.

Thus, according to the invention, there is provided a compound of formula I,

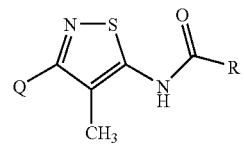

or a pharmaceutically acceptable salt thereof, wherein
Q is a phenyl group of formula Q$^A$

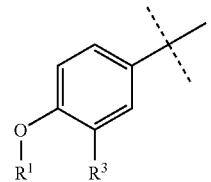

in which R$^1$ is methyl or ethyl, and R$^3$ is hydrogen or fluoro; or
Q is a phenyl group of formula Q$^B$

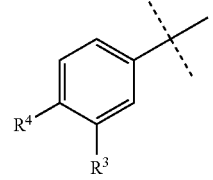

in which
R$^3$ is hydrogen or fluoro, and R$^4$ is hydrogen, fluoro, chloro or bromo; or each of R$^3$ and R$^4$ is chloro; or R$^3$ is hydrogen and R$^4$ is methylthio or 1,1-difluoroethyl; and
R—CO is (R,R)-trans-2-methylcyclopropanecarbonyl.

As used herein, the expression a compound of formula I or the expression a compound of the invention includes the compound, as well as a pharmaceutically acceptable salt of said compound. When used in this specification, unless otherwise defined, the following terms have the meanings given: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

While the R—CO group of the instant invention is chiral, the compound of formula I may be present in a mixture with its enantiomer, such as a racemic mixture, and/or with either of the cis-diasteriomers. Preferably, the compound of the invention is the substantially pure (R,R)-isomer with an enantiomeric excess of, for example, 95% or greater. As noted below, the compound of formula I, or a pharmaceutically acceptable salt thereof, may exhibit polymorphism and/or may form a solvate with water or an organic solvent. The present invention also encompasses any such polymorphic form, any solvate or any mixture thereof.

A particular value for Q is 4-methoxyphenyl, 3-fluoro-4-methoxyphenyl, 4-ethoxyphenyl, phenyl, 4-fluorophenyl, 4-chlorophenyl, 4-bromophenyl, 3,4-dichlorophenyl, 4-(methylthio)phenyl or 4-(1,1-difluoroethyl)phenyl.

A particular compound of formula I is one wherein Q is $Q^A$.

Another particular compound of formula I is one wherein Q is $Q^B$, and, more particularly wherein $R^4$ is chloro.

For any of the above compounds, a particular value of $R^3$ is hydrogen.

When Q is $Q^B$, $R^4$ is chloro and $R^3$ is hydrogen, the compound of formula I is (R,R)—N-[3-(4-chlorophenyl)-4-methylisothiazol-5-yl]-2-methylcyclopropane-carboxamide (or a pharmaceutically acceptable salt thereof).

A preferred compound of formula I is (R,R)—N-[3-(4-methoxyphenyl)-4-methyl-isothiazol-5-yl]-2-methylcyclopropanecarboxamide, or a pharmaceutically acceptable salt thereof.

A pharmaceutically acceptable salt of a compound of the invention is one which is the acid addition salt of the compound of formula 1 with an organic or inorganic acid which affords a physiologically acceptable anion.

As an additional aspect of the invention there is provided a pharmaceutical composition comprising a compound of formula I, or a pharmaceutically acceptable salt thereof, as provided in any of the descriptions herein together with a pharmaceutically acceptable diluent, excipient or carrier.

Further, there is provided a pharmaceutical composition for treating pain, particularly chronic pain, containing as an active ingredient a compound of formula I, or a pharmaceutically acceptable salt thereof, as provided in any of the descriptions herein.

A pharmaceutical composition comprising a compound of formula I may be prepared by a conventional method, which may include control of the particle size, such as micronization, or the use of a nanodispersion. Preferably, the pharmaceutical composition is a composition suitable for oral administration.

A compound of formula I may be prepared by processes which include processes known in the chemical art for the production of structurally analogous compounds or by a novel process described herein. A novel process described herein provides another aspect of the invention. A process for the preparation of a compound of formula I, or a pharmaceutically acceptable salt thereof, and novel intermediates for the manufacture of a compound of formula I provide further features of the invention and are illustrated by the following procedures in which the meaning of the generic radicals are as defined above, unless otherwise specified.

Thus, there is provided a process for preparing a compound of formula I, or a pharmaceutically acceptable salt thereof, as provided in any of the above descriptions comprising the step selected from (A) acylating an amine of formula II,

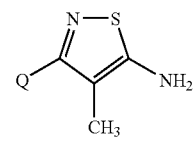

II using an acid of formula HOOC—R, or an activated derivative thereof;

(B) for a compound of formula I in which Q is $Q^A$, alkylating the phenolic oxygen of a compound of formula III

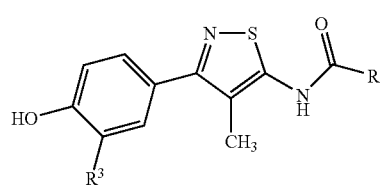

III in which $R^3$ is hydrogen or fluoro, using a reagent of formula $R^1$—Y in which Y is a conventional leaving group for nucleophilic substitution; and (C) methylating a corresponding compound of formula VI

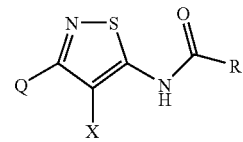

VI in which X is bromo or iodo;

whereafter, for any of the above procedures, when a pharmaceutically acceptable salt of a compound of formula I is required, it is obtained by reacting the basic form of the compound of formula I with an acid affording a physiologically acceptable counterion or by any other conventional procedure;

and wherein, unless otherwise specified above, Q, R—CO and $R^1$ have any of the values defined hereinabove.

Thus, as an aspect of the invention, there is provided a compound selected from:

(a) an amine of formula II,

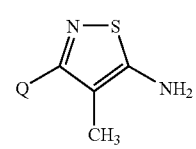

II (b) a compound of formula III

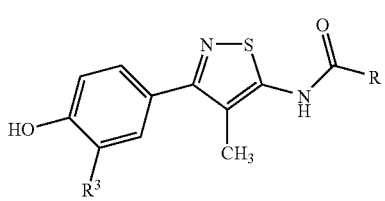

in which R³ is hydrogen or fluoro, and
(c) a compound of formula VI

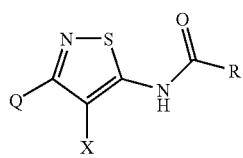

in which X is bromo or iodo,
wherein, unless otherwise specified, Q and R—CO have any of the values defined hereinabove.

For an acid of formula HOOC—R, a typical activated derivative includes an ester (particularly a lower alkyl ester such as the methyl or ethyl ester or the benzyl ester), an acid halide (particularly the acid chloride) and an activated ester or anhydride (including the 4-nitrophenyl ester and an activated ester or anhydride derived from a coupling reagent). With a lower alkyl ester or the benzyl ester, the acylation may be carried out using, for example, trimethylaluminum or potassium t-butoxide.

As used herein, a leaving group "Y" is a moiety which is displaced in a nucleophilic substitution reaction, for example a halo group (such as bromo or iodo), a sulfonate ester group (such as methylsulfonyloxy, p-toluylsulfonyloxy or trifluoromethyl-sulfonyloxy, and more particularly, for methylation, methoxysulfonyloxy), or the reactive species of a Mitsunobu reaction, such as the one derived from treating an alcohol with triphenylphosphine, diethyl azodicarboxylate and triethylamine.

For methylating a compound of formula VI in which X is bromo or iodo, a Stille coupling procedure using, for example, tetramethyltin and a Stille catalyst, such as bis(triphenylphospine)palladium(II) chloride, in dimethylformamide, may be employed; or, alternatively, a trans-metalation-methylation procedure, using, for example, butyllithium followed by methyl iodide in tetrahydrofuran, may be employed.

An acid of formula HOOC—R may be obtained by using a published procedure. Conveniently, an acid of formula HOOC—R is obtained by a procedure described in the preparations below. Conveniently, the acid of formula HOOC—R is resolved as a salt, preferably, as (S)-2-amino-3-phenyl-1-propanol (R,R)-2-methylcyclopropanecarboxylic:acid (1:1) salt, more preferably in crystalline form, which provides a further aspect of the invention. Thus, there also is provided the process described hereinabove wherein the acid of formula HOOC—R, or an activated derivative thereof, is obtained by using conventional methodology from (S)-2-amino-3-phenyl-1-propanol (R,R)-2-methyl-cyclopropanecarboxylic acid (1:1) salt.

An amine of formula II,

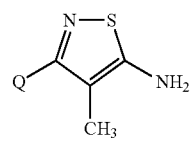

conveniently is obtained by a procedure described below. Generally, a benzonitrile of formula Q-CN is condensed with propionitrile to provide a nitrile of formula IV,

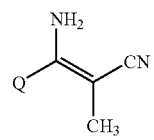

which is converted into the thioamide of formula V,

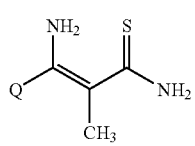

conveniently using thioacetamide. Oxidation of the thioamide of formula V, conveniently using hydrogen peroxide, affords the 5-aminoisothiazole of formula II.

A compound of formula III

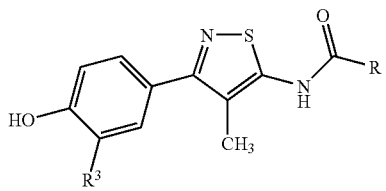

in which R—CO is (R,R)-trans-2-methylcyclopropanecarbonyl and R³ is hydrogen or fluoro provides another aspect of the invention, and it may be obtained by acylating the corresponding amino phenol of formula IIa

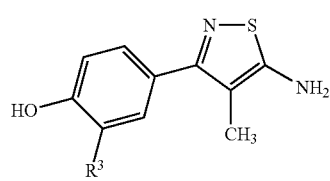

using an acid of formula HOOC—R, or an activated derivative thereof. The compound of formula IIa may be obtained by removal of the O-protecting group from a corresponding compound in which the phenolic oxygen is protected by an O-protecting group. Conveniently, the compound of formula IIa is obtained by O-demethylation of the corresponding methoxy compound of formula II. A particular compound of formula III is (R,R)—N-[3-(4-hydroxyphenyl)-4-methyl-isothiazol-5-yl]-2-methylcyclopropane-carboxamide.

A compound of formula VI in which X is bromo or iodo may be obtained by brominating or iodinating a corresponding compound of formula VII.

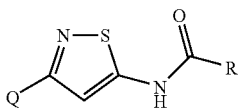

VII

The compound of formula VII conveniently is obtained by acylating the corresponding amine of formula VIII,

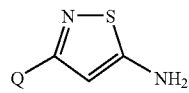

VIII using an acid of formula HOOC—R, or an activated derivative thereof.

The amine of formula VIII may be prepared using a similar procedure to that described for the preparation of an amine of formula II, but beginning with the benzonitrile of formula Q-CN and acetonitrile to afford a nitrile of formula IX,

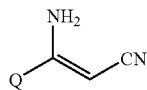

IX which is converted into a thioamide of formula X,

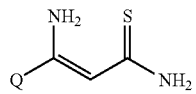

X and oxidatively cyclized to afford the amine of formula VIII.

Alternatively, the thioamide of formula X, may be treated with two equivalents (or slightly more, such as 2.2 equivalents) of bromine to effect both cyclization and bromination to afford an amine of formula VIIIa,

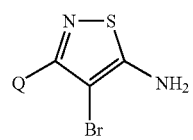

VIIIa which is acylated using an acid of formula HOOC—R, or an activated derivative thereof, to afford the corresponding compound of formula VI in which X is bromo.

A further alternative preparation of a compound of formula VI in which X is bromo is as follows. Acylating 3,4-dibromoisothiazol-5-ylamine, formula XI,

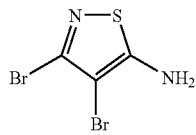

XI using an acid of formula HOOC—R, or an activated derivative thereof, affords the corresponding compound of formula XII,

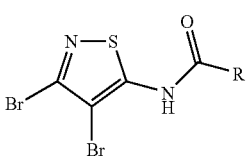

XII which is cross-coupled with a boronic acid of formula Q-B(OH)$_2$ to provide the compound of formula VI in which X is bromo.

The relative potency and selectivity of compounds of the instant invention for mGlu$_1$ receptors is evaluated using stable clonal cell lines expressing recombinant mGlu$_{1, 2, 3, 4, 5 \text{ or } 8}$ receptors transfected into AV12 cell lines containing the rat EAAT1 glutamate transporter (RGT) cells.

For example, in more detail, compounds of the present invention are evaluated for effects on glutamate induced calcium flux responses using an AV-12 cell line expressing human recombinant mGlu$_{1a}$ receptor protein (see Kingston et al. Neuropharmacology. 37(1):1-12, 1998). mGlu$_1$ receptor mediated responses are determined by changes in intracellular calcium concentrations measured by a fluorescent calcium sensitive dye Fluo-3. Cells are harvested and seeded into 96 well microtiter plates. After 48 h incubation in a humidified incubator at 37° C., the cells are loaded with 10 μM Fluo-3 AM dye for 60 min at 25° C. Unincorporated extracellular dye is removed from the wells by washing with buffer solution, and plates are then transferred to a 96-channel fluorimetric imaging plate reader (FLIPR-Molecular Devices Corporation, La Jolla, Calif., USA). Baseline fluorescence readings are undertaken for 10 sec prior to addition of test compounds by an automatic pipetting device integral to the FLIPR instrument. Following a 20 sec delay, glutamate is then added to the wells at an EC90% concentration (10 μM); and changes in fluorescence are monitored over 60 sec. The inhibitory effects of the compounds are determined by comparing the peak fluorescence response to glutamate in the presence and absence of compound. IC$_{50}$ values are calculated using a 4 parameter logistic curve fitting program (GraphPad Prism™ V4 or Activity Base™ V5.3 software). Compounds exemplified herein exhibit an IC$_{50}$ of less than 100 nM. For example, the each of the compounds of Example 1 and Example 6 has an IC$_{50}$ measured in the above screen as less than 20 nM.

A similar assay using the rat mGlu$_1$ receptor may be carried out to further characterize a compound in conjunction with in vivo screens run in the rat.

Compounds of the invention have demonstrated in vivo activity in rat pain models. These well known pain models conveniently may be carried out as summarized below. For example, at doses in which no deficit in performance are noted in the rotorod test, which may be carried out as described below, the compound of Example 1 demonstrates dose-dependent activity in fasted male Harlan Sprague Dawley rats (HSD, 200-250 g) in the formalin, carrageenan, capsaicin and tail flick models and in non-fasted male HSD rats (300-350 g) for the L5/L6 spinal nerve ligation model. All data are analyzed by ANOVA and Dunnett's t-test using JMPv4.1 (SAS Institute Inc., Cary, N.C.) statistical software unless otherwise indicated. Data are expressed as means±SEM. Specific conditions for each model are briefly described.

Formalin model: Drug is administered prior to formalin (50 µl, 5%), injected s.c. into the dorso-lateral surface of the right hindpaw. Paw-licking behavior is measured in an automated assay, as number of events, from 0-50 minutes after formalin. Data are expressed as paw-licking pain behavior events in early phase (0-5 minutes) or late phase (15-40 minutes). In this model the compound of Example 1 demonstrates dose dependent attenuation of late phase pain behavior in fasted rats when administered at 3 to 60 mg/kg, p.o., 1 hour prior to formalin and the compound of Example 6 demonstrates dose dependent attenuation when administered at 1 to 30 mg/kg.

L5/L6 Spinal Nerve ligation model: Tight ligation is performed on L5 and L6 spinal nerves (one side only). Two weeks later, mechanical allodynia behavior is measured using von Frey filaments using incremental bending forces (0.5-15 g) at various time points after drug administration.

Carrageenan model: Carrageenan (100 µl, 3%) is injected into the plantar surface of the right paw, and drug is administered two hours after carrageenan. Thermal hyperalgesia is measured using a radiant heat source, with a 30 second cut off to prevent tissue damage. Paw withdrawal latency in seconds is measured as the difference between the inflamed paw and the non-inflamed left paw.

Capsaicin model: Drug is administered prior to capsaicin. Capsaicin (25 µl, 30 µg) in olive oil is injected into the plantar surface of the right paw. Mechanical allodynia behavior is measured using von Frey filaments using incremental bending forces (0.5-15 g) at 15 minutes and 1 hour after capsaicin.

Tail Flick model: Radiant heat source at base of tail with 10 sec cut off is used to elicit tail flick response at various time points after drug administration.

Rotorod test: Male Sprague Dawley rats (180-230 g, Harlan labs, Indianapolis) are used for the rotorod test. The ability of mGlu1 antagonists to induce sedation/ataxia is examined using an automated accelerating rotorod (Omnitech Electronics Inc., Columbus, Ohio) connected to an IBM PC computer as described previously (Simmons et al., Neuropharmacol. (1998) 37, 25-36). Rotorod testing is conducted prior to drug administration and again at 1, 2, 3 and 4 hours after oral administration of, for example, 60 mg/kg of drug in fasted rats. The time points chosen correspond to behavioral testing in the pain models. Animals that maintain posture and do not fall off the rotorod are given a maximum score of 40 seconds. Data are analyzed by ANOVA and Dunnett's t-test using JMPv4.1 (SAS Institute Inc., Cary, N.C.) statistical software. Data are expressed as means±SEM.

Thus, a compound of the invention is expected to be useful whenever antagonism of the mGlu$_1$ receptor is indicated. In particular, a compound of the invention is expected to be useful for the treatment of pain, particularly chronic pain (or persistent pain), for example chronic neuropathic pain, chronic inflammatory/joint related pain, or chronic non-inflammatory/non-neuropathic pain (NINN pain), as well as for treatment of migraine or epilepsy. Accordingly, one particular aspect of the invention is treatment of chronic neuropathic pain; another particular aspect of the invention is treatment of chronic inflammatory/joint related pain; and a further particular aspect of the invention is treatment of chronic non-inflammatory/non-neuropathic pain. Neuropathic pain includes pain associated with diabetic peripheral neuropathy and postherpetic neuralgia. In addition, a compound of the invention may have utility as an agent in the treatment of seizures in epilepsy or as an agent in the treatment of anxiety, as well as utility as a neuroprotective agent following cerebral infarction.

Thus, as another aspect of the invention, there is provided a method of treating pain, particularly chronic pain, in a mammal, particularly a human, in need of treatment comprising administering to the mammal an effective amount of a compound of formula I, or a pharmaceutically acceptable salt thereof, wherein Q and R have any of the values defined hereinabove. The mammal in need of treatment also may be a domestic animal, such as a horse, or a companion animal, such as a cat or a dog.

Also, there is provided a compound of formula I according to any of the definitions herein, or a pharmaceutically acceptable salt thereof, for use as a medicament.

Further, there is provided a compound of formula I, or a pharmaceutically acceptable salt thereof, wherein Q and R have any of the values defined hereinabove, for use in treating pain, particularly chronic pain.

In addition, there is provided the use of a compound of formula I, or a pharmaceutically acceptable salt thereof, wherein Q and R have any of the values defined hereinabove, for the manufacture of a medicament for treatment of pain, particularly chronic pain.

For any of the above statements, a particular form of chronic pain is neuropathic pain. Another particular form of chronic pain is chronic inflammatory/joint related pain. A further particular form of chronic pain is chronic non-inflammatory/non-neuropathic pain (NINN pain).

The specific dose of a compound of the invention to be administered to a patient will, of course, be determined by the circumstances surrounding the case, including, for example, the compound administered, the rate of administration and the condition being treated. A typical daily dose for the treatment of chronic pain may be between 1 and 300 mg/day, more particularly between 5 and 200 mg/day, administered in a single dose or in two or more divided doses, preferably via oral administration. Thus, a compound of the invention may be used in treating existing pain or in prophylactic treatment.

In the following illustrative preparations and examples, the following meanings and abbreviations are used throughout: R—CO is (R,R)-trans-2-methyl-cyclopropanecarbonyl; DMF, dimethylformamide; DMSO, dimethyl sulfoxide (perdeuterated [–d$_6$] if for NMR); equiv, equivalent(s); ES-MS, electrospray ionization mass spectrum; EtOAc, ethyl acetate; FID, flame ionization detection; GC, gas chromatography; HPLC, high pressure liquid chromatography; LCMS, liquid chromatography coupled mass spectrum; MeOH, methanol; MTBE, methyl t-butyl ether; NMR, nuclear magnetic resonance spectroscopy or spectrum; TEA, triethylamine; TFA, trifluoroacetic acid; THF, tetrahydrofuran; TLC, thin layer chromatography; UV, ultraviolet (detection); ca., about; ee, enantiomeric excess; Ph, phenyl; satd, saturated. Reagents were obtained from a variety of commercial sources. Solvents are generally removed under reduced pressure (evaporated). In some preparations indicated yields are representative crude yields for products which are isolated by evaporation or filtration and used directly without further purification.

Preparation of Benzyl (R,R)-2-Methylcyclopropanecarboxylate:

A 2.0 M oxalyl chloride in dichloromethane solution is prepared by adding with stirring 98% oxalyl chloride (110.0 mL) to anhydrous dichloromethane (600.0 mL). The resulting solution of oxalyl chloride (1.20 mol) is added dropwise over 1 h to a stirring solution of 2-methylcyclopropanecarboxylic acid (commercially available product which is a cis-trans mixture, 120.0 g, 1.20 mol) in toluene (800.0 mL) containing DMF (0.6 mL, 7.8 mmol). The mixture is stirred 2 h at room temperature; then it is added dropwise to a solution of benzyl alcohol (114.0 mL, 1.10 mol), anhydrous THF (800.0 mL), and pyridine (194.0 mL, 2.41 mol) over 1.5 h. The mixture is stirred 1 h longer after addition, partitioned between ethyl acetate (2 L) and 10% aqueous potassium carbonate (2 L); and the organic phase is washed (10% aqueous potassium carbonate (2 L) and brine (2 L)), dried ($MgSO_4$) and evaporated to a liquid. Chromatography over silica gel, eluting with 5% ethyl acetate in hexanes, provides the major product, racemic benzyl trans-2-methyl-cyclopropanecarboxylate as a clear, colorless liquid (193.8 g, 93%).

$^1$H NMR (DMSO-$d_6$) δ 7.38 (m, 5H), 5.05 (s, 2H), 1.42 (m, 1H), 1.30 (m, 1H), 1.06 (d, J=6.0 Hz, 3H), 1.04 (m, 1H), 0.74 (m, 1H).

The racemic ester (189 g) is separated by chiral HPLC: Preparative Conditions: Steady-State Recycle Method using: Column: Chiralcel OJ, 8×32 cm; Fluent: 10/90 isopropanol/heptane; Flow Rate: 375 mL/min; Visualization: UV at 220 nm; Cycle Time: about 7.1 min; Loading: about 21 mL/injection (0.5 g Loading) with sample dissolved in eluent at 0.025 mg/mL to afford benzyl (R,R)-trans-2-methylcyclopropanecarboxylate (73 g) in greater than 99.7% ee by chiral HPLC, Analytical Conditions: Chiralcel OJ. 4.6×250 mm; Fluent: 10/90 isopropanol/heptane; Flow Rate 1.0 mL/min; Visualization: UV at 220 nm; Retention times: 6.5 min and 7.2 min.

Alternative Preparation of Benzyl (R,R)-2-Methylcyclopropanecarboxylate:

A mixture of 2-methylcyclopropanecarboxylic acid (commercial product which is a cis-trans mixture, 75.0 g, 0.75 mol) and 1 N NaOH (900 mL, 0.90 mol) is warmed and stirred at 45° C. To the stirring solution is added benzyl bromide (131.0 mL, 1.10 mol) and methyltrialkyl($C_8$-$C_{10}$)ammonium chloride (Adogen™ 464, 37.5 g). The mixture is stirred at 40-45° C. for 4 h, cooled to room temperature, and extracted with ethyl ether (800 mL). The organic layer is dried ($MgSO_4$) and evaporated to a liquid. Chromatography over silica gel, eluting with hexanes gradually increasing to 5% ethyl acetate in hexanes, provides the racemic benzyl trans-2-methylcyclopropanecarboxylate as a liquid (132.2 g, 93%); $^1$H NMR (DMSO-$d_6$) δ 7.40 (m, 5H), 5.05 (s, 2H), 1.43 (m, 1H), 1.30 (m, 1H), 1.06 (d, J=6.0 Hz, 3H), 1.02 (m, 2H), 0.74 (m, 1H). [Note: If NMR reveals the presence of a minor amount of cis isomer, it is removable by the chiral HPLC separation which may be carried out as described above.]

Preparation of (R,R)-2-Methylcyclopropanecarboxylic Acid, also Described as (R,R)-trans-2-Methylcyclopropanecarboxylic Acid:

A. Preparation of Racemic 2-Methylcyclopropanecarboxylic Acid:

i. Dimethyloxosulfonium Methylide (Solution in DMSO):

To a stirred suspension under nitrogen of trimethylsulfoxonium iodide (2.47 kg, 1.05 equivalent) in DMSO (8.00 L) is added potassium hydroxide (90% by weight, 0.69 kg, 1.05 equivalent) portion wise in 100 g portions. (Alternatively, the base may be added all at once, in which case an exotherm occurs.) Additional DMSO (4.00 L) is added and the reaction mixture is stirred at ambient temperature until the mixture becomes homogeneous (except for some undissolved KOH pellets, which are not added in the following step) and ylide formation is complete (about 2-2.5 h).

ii. Ethyl 2-Methylcyclopropanecarboxylate:

To a solution of ethyl trans-crotonate (1.20 kg, 1.31 L, 1.00 equivalent) in DMSO (3.00 L) at ambient temperature is added the above preformed ylide solution over 30 min, while the temperature of the reaction mixture is maintained at about 15-20° C. The progress of the reaction is followed by analysis by gas chromatography (GC, conditions below) until only a small amount of residual crotonate relative to the 2-methyl-cyclo-propanecarboxylate is observed (about 20-24 h). The reaction mixture is split into two equal (8.5 L) portions for work-up; each portion is treated as follows: Methyl t-butyl ether (MTBE, 6 L) is added, and the biphasic mixture is cooled to 15° C. before the dropwise addition of water (6 L) over about 45 min while maintaining the temperature below 23° C. After the phases are separated, the organic phase is washed twice with 10% brine; and the solvent is gently removed under vacuum (400 mbar, bath temperature 35° C.) to afford the ethyl 2-methylcyclopropanecarboxylate (1.00 kg, 26.8%) containing about 3.3 equivalents of MTBE.

GC method: column: Varian VF-1 ms, length: 60 m, diameter 320 μm, thickness: 1 μm; gas: helium; T°: from 80 to 300° C. over 35 min; run time: 35 min; detection: FID; sample directly diluted in methanol.

iii. 2-Methylcyclopropanecarboxylic Acid:

The above mixture containing ethyl 2-methylcyclopropanecarboxylate (1.00 kg, 1.00 mol, 1.00 equivalent) is combined with water (4.00 L) and 10.4 M sodium hydroxide solution (0.32 L, 1.20 equivalent), and the mixture is heated to 46° C. as the MTBE is gradually distilled. (If ester is found in a distillate fraction of MTBE by analysis by gas chromatography, it is returned to the reaction mixture; and the MTBE is again distilled.) When analysis by gas chromatography shows no remaining ester in the reaction mixture (about 1-4 h), it is cooled to 20° C., the distillate and additional MTBE (2 L) are added, and the layers are separated. The aqueous phase is acidified with 12.18 M hydrochloric acid and extracted with MTBE (3×4 L). The MTBE is carefully distilled under vacuum (for example, 400 mbar, then 200 mbar, bath temperature 35° C.) from the combined organic extracts to afford racemic 2-methylcyclopropanecarboxylic acid containing a small amount of residual MTBE, which is used directly for resolution. (Analysis of a typical preparation by gas chromatography and NMR shows a yield of 0.99 equivalents racemic 2-methylcyclopropanecarboxylic acid containing 1.7% cis-isomer and 0.3 equivalents MTBE.)

B. Preparation of (S)-2-Amino-3-phenyl-1-propanol (R,R)-2-methylcyclopropane-carboxylic acid (1:1) salt, also described as (R,R)-2-methylcyclopropanecarboxylic acid (S)-phenylalaninol (1:1) salt:

Racemic trans-2-methylcyclopropanecarboxylic acid (20 g, 0.2 mol) is dissolved in ethyl acetate (200 mL). (S)-2-Amino-3-phenyl-1-propanol [also known as (S)-phenylalaninol] (15.6 g, 0.103 mol, 0.51 equiv) is added in one portion, and the mixture heated to 65-70° C. After crystallization, which may be facilitated by seeding, the suspension is stirred at room temperature 20 h, then filtered; and the crystals are washed with ethyl acetate (2×15 mL). The crystals are dried at 40° C. under vacuum for 3 h: mass 18.4 g (37% molar yield, enantiomeric composition by chiral GC=85/15, chiral GC method below). The crystals are re-suspended in 370 mL ethyl acetate; the suspension is heated to reflux for 1 h, cooled to room temperature overnight, and the crystals filtered, washed and dried as above: mass 16.7 g (91% yield, chiral composition 96/4). A second purification in ethyl acetate (170 mL) as above affords (S)-2-amino-3-phenyl-1-propanol (R,R)-2-methylcyclopropanecarboxylic acid (1:1) salt (16.12 g, 96.5% yield, chiral composition 99/1=98% ee; 32% overall yield from racemic trans-2-methylcyclopropanecarboxylic acid).

$^1$H NMR (400 MHz, DMSO): δ 0.47 (m, 1H), 0.84 (m, 1H), 1.01 (d, 3H), 1.07 (m, 2H), 2.5 (m, 1H), 2.7 (m, 1H), 3.0 (m, 1H), 3.25 (dd, 1H), 3.35 (d, 2H), 5.0-5.2 (br, 4H), 7.2 (m, 3H), 7.3 (dd, 2H); mp of the salt (98% ee) 130-131° C.

Chiral GC method: Column: Hydrodex B-PM; carrier gas: helium; Injector T°: 200° C.; pressure: 30 psi; split ratio: 1/100; detection: FID, 230° C.; flow: 50 mL/min; injection volume: 1 microL: initial T°: 130° C. Retention time of R,R-enantiomer: 8.3 min (8.08 min for S,S-enantiomer).

Sample preparation: The salt (ca. 10 mg) is dissolved in 1 N HCl (ca. 1 mL) and the free acid extracted with ethyl acetate (ca. 1 mL). The ethyl acetate extract is directly injected in GC.

C. Preparation of (R,R)-2-Methylcyclopropanecarboxylic Acid:

To (S)-2-amino-3-phenyl-1-propanol (R,R)-2-methylcyclopropanecarboxylic acid (1:1) salt (12.6 g, 0.05 mol) is added 1 N aqueous HCl (100 mL, 0.1 mol). After 10 min stirring, the solution is extracted with ethyl acetate (2×50 mL). The organic extracts are dried (MgSO$_4$) and concentrated under vacuum (40-45° C./200 mbar) to afford (R,R)-2-methylcyclopropanecarboxylic acid (5 g, 100%) as a colorless oil.

$^1$H NMR (400 MHz, CDCl$_3$): δ 0.75 (m, 1H); 1.1 (d, 3H); 1.2 (m, 1H); 1.3 (m, 1H); 1.42 (m, 1H); 11.0 (br, 1H).

Telescoped Preparation of (R,R)-2-Methylcyclopropanecarboxylic Acid for formation of (S)-2-Amino-3-phenyl-1-propanol (R,R)-2-methylcyclopropanecarboxylic Acid (1:1) Salt:

i. Dimethyloxosulfonium Methylide (Solution in DMSO):

To a stirred suspension under nitrogen of trimethylsulfoxonium iodide (1.18 equivalent) in DMSO (about 3.3 mL per g of iodide) is added potassium t-butoxide (1.05 equivalent) at once. An exotherm occurs. The reaction mixture is stirred at 20-35° C. until the mixture becomes homogeneous and ylide formation is complete.

ii. Ethyl 2-Methylcyclopropanecarboxylate:

A solution of ethyl trans-crotonate (1.00 equivalent) in DMSO (3 mL per g of ester) is heated to 80° C. To that solution, is added slowly, the above preformed ylide solution while the temperature of the reaction mixture is maintained at 80° C. After a typical addition/reaction time of one hour, analysis by gas chromatography (as above) shows only a small amount of residual ethyl crotonate relative to the ethyl 2-methyl-cyclopropanecarboxylate.

iii. 2-Methylcyclopropanecarboxylic Acid:

The above reaction mixture is cooled to 20° C., and aqueous KOH (5% w/w, about 1.14 equivalents of KOH) is added over 15 min while maintaining the temperature of the reaction mixture at 20-30° C. Stir the reaction mixture a further 2 to 3 h (until no residual ester is indicated by gas chromatography (as above). The resulting solution (pH about 12 by pH paper) is acidified to pH 2-3 at 20-30° C. by the slow addition of 1.5 N HCl; then it is extracted with three portions of isopropyl acetate (each portion 5 mL per gram of starting ethyl trans-crotonate). The combined organic phase is washed with 15% brine and partially evaporated by distilling under a vacuum of 100-300 mbar with a bath temperature of 45° C. (and rediluted with isopropyl acetate, if necessary) to provide a solution corresponding to about 10 mL per calculated g of 2-methylcyclopropane-carboxylic acid for use in resolution using a similar procedure to that described above.

Alternative Preparation of (R,R)-2-Methylcyclopropanecarboxylic Acid:

Under a nitrogen atmosphere, hexyllithium (2.3 M in hexanes, 8 mL, 18.4 mmol) is added dropwise over 20 min to triethyl phosphonoacetate (4.5 g, 19.67 mmol) in anhydrous 2-methyltetrahydrofuran (40 mL) keeping the temperature between 19 and 25° C. After 30 min, (S)-propylene oxide (1.17 g, 20.15 mmol) is added, and the mixture transferred into a 160 mL Stainless Steel pressure (Parr) reactor. The mixture is heated to 150° C. within 15 min and stirred at this temperature ° for 16 h. (NMR analysis of the crude mixture indicates >95% conversion to ethyl (R,R)-2-methylcyclopropane-carboxylate.)

Water (50 mL) and 30% aqueous NaOH (25 mL) are added, and the biphasic mixture is stirred at reflux for 5 h. The layers are separated and the organic phase discarded. 37% aqueous HCl (25 mL) is added to the aqueous layer, and the mixture is extracted with isopropyl acetate (2×50 mL). The organic layer, containing (R,R)-2-methylcyclopropanecarboxylic acid, is washed with 10% aqueous NaCl (3×25 mL) and partially evaporated under vacuum to a total mass of 14.5 g before (S)-2-amino-3-phenyl-1-propanol [also known as (S)-phenylalaninol] (3.01 g, 19.91 mmol) is added in one portion, causing spontaneous crystallization of (S)-2-amino-3-phenyl-1-propanol (R,R)-2-methylcyclopropanecarboxylic acid (1:1) salt. The suspension is stirred overnight. The crystals are filtered, washed with isopropylacetate (4 mL) and dried at 40° C. under vacuum to afford (S)-2-amino-3-phenyl-1-propanol (R,R)-2-methylcyclopropanecarboxylic acid (1:1) salt (3.4 g, 69% overall yield). Chiral GC: >99.5% ee, 98% de. (Alternatively, the acid may conveniently be isolated as the dicyclohexylamine (1:1) salt.)

The salt may be converted into (R,R)-2-methylcyclopropanecarboxylic acid using a procedure similar to the one described above.

Preparation of a Nitrile of Formula IV

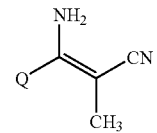

IV

Except as otherwise described, a nitrile of formula IV, having the indicated value of Q, is prepared using the corresponding benzonitrile of formula Q-CN and propionitrile and a similar procedure to that of Preparation IV-1, below.

Preparation IV-1, Q=4-Methoxyphenyl:

Combine 4-methoxybenzonitrile (50.0 g, 376 mmol), potassium t-butoxide (84.2 g, 752 mmol), propionitrile (62.0 g, 1.130 mmol) and toluene (1,880 mL); and stir for 72 h. Dilute with satd NaHCO$_3$ and extract with EtOAc. Evaporate the organic solution and crystallize from hexane/EtOAc to afford 3-amino-3-(4-methoxyphenyl)-2-methylacrylonitrile. Yield: 35.1%. ES-MS: m/e 189.2 (m+1).

Preparation IV-6, Q=4-Chlorophenyl:

In a 2 L round bottom flask (fitted with rubber septum, nitrogen blanket and stir bar) combine 4-chlorobenzonitrile (60.0 g, 1.00 equiv, 432 mmol), propionitrile (61.2 mL, 2.00 equiv, 864 mmol), tetrahydrofuran (43.2 mL) and 1.0 M potassium t-butoxide in t-butanol (tert-butyl alcohol, potassium derivative, 475 mL, 1.10 equiv; 475 mmol); and stir for 24 h. Quench with aqueous NaHCO$_3$ and extract with ethyl acetate. Wash the organic phase 2 times with brine, dry (K₂CO₃), filter, and concentrate to dryness. Purify by flash chromatography on silica, eluting with 15:85 to 50:50 ethyl acetate/hexane, to afford 3-amino-3-(4-chlorophenyl)-2-methylacrylonitrile (as an uncharacterized E-/Z-mixture). Yield: 49.5%. LCMS: 193.0 (m+1).

Preparation IV-7, Q=4-Bromophenyl: 3-amino-3-(4-bromophenyl)-2-methyl-acrylonitrile.

Preparation of a Thioamide of Formula V

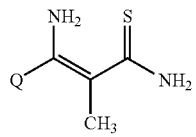

V

Except as otherwise described, a thioamide of formula V, having the indicated value of Q, is prepared using the corresponding nitrile of formula IV and a similar procedure to that of Preparation V-1, below.

Preparation V-1, Q=4-Methoxyphenyl:

Add HCl (4 N in dioxane, 659 mL, 2.640 mmol) to a solution of 3-amino-3-(4-methoxyphenyl)-2-methylacrylonitrile (24.8 g, 132 mmol), thioacetamide (19.8 g, 264 mmol) and dioxane (132 mL) under dry nitrogen. Stir for 2 h. Evaporate, dilute the solid with dioxane (20 mL) and add dry TEA (40 mL). Add satd K₂CO₃ and extract with EtOAc. Evaporate the organic solution and crystallize from CHCl₃/hexane (95/5); then recrystallize from MeOH/H₂O to remove the excess thioacetamide to afford 3-amino-3-(4-methoxyphenyl)-2-methyl-thioacrylamide. Yield: 90.8%.

Preparation V-6, Q=4-Chlorophenyl:

Add hydrogen chloride (4 M in 1,4-dioxane, 858 mL, 16.0 equiv; 3.43 mol) to an E-/Z-mixture of 3-amino-3-(4-chlorophenyl)-2-methylacrylonitrile (41.3 g, 1.00 equiv, 214.4 mmol) and thioacetamide (32.71 g, 2 equiv, 2.00 equiv; 428.8 mmol) in a 2 L round bottom flask RBF (fitted with rubber septum, nitrogen blanket, stir bar and cooling bath). Maintain a solution temperature below 30° C. with an ice bath until the addition is complete. Remove the ice bath, stir for 2 h, and slowly add the mixture to 1.5 L of 30% aqueous NH₄OH in an ice bath with stirring. Extract the mixture 2 times with ethyl acetate. Wash the organic phase 2 times with brine, dry (K₂CO₃), filter, and concentrated to dryness. Crystallize the mixture from hexane and chloroform (10/90). Triturate the resulting solid from ethanol and water (10/90) to afford 3-amino-3-(4-chlorophenyl)-2-methyl-thioacrylamide (as an uncharacterized E-/Z-mixture). Yield: 82.3%. ¹H NMR (CD₃OD) δ 9.95 (s, 2H), 8.74 (s, 1H), 8.29 (d, J=6.0 Hz, 2H), 8.25 (s, 1H), 8.11 (d, J=6.0 Hz, 2H), 4.099 (s, 3H).

Preparation V-7, Q=4-Bromophenyl: 3-amino-3-(4-bromophenyl)-2-methyl-thioacrylamide.

Preparation of an Amine of Formula II

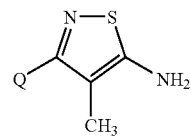

II

Except as otherwise described, an amine of formula II, having the indicated value of Q, is prepared using the corresponding thioamide of formula V and a similar procedure to that of Preparation II-1, below.

Preparation II-1, Q=4-Methoxyphenyl:

Add hydrogen peroxide (30% by weight, 2.39 g, 70.3 mmol) to a solution of 3-amino-3-(4-methoxyphenyl)-2-methyl-thioacrylamide (7.800 g, 35.135 mmol) in methanol (703 mL). Stir 3 h. Quench the reaction with Na₂S₂O₃ (20% in water) and evaporate to 10 mL. Dilute with EtOAc (500 mL) and wash the organic phase with brine (3×100 mL), evaporate and crystallize from EtOAc/hexane to afford 3-(4-methoxy-phenyl)-4-methylisothiazol-5-ylamine. Yield: 88.2%. ES-MS: m/e 221.0 (m+1).

Preparation II-6, Q=4-Chlorophenyl:

In a 2 L round bottom flask (fitted with stir bar) combine (E/Z)-3-amino-3-(4-chlorophenyl)-2-methyl-thioacrylamide (40.0 g, 1.00 equiv, 176 mmol), methanol (882 mL, 21.80 mol) and hydrogen peroxide (30% by weight, 14.2 mL, 1.40 equiv, 247 mmol). Stir for 2 h, then quench the reaction with Na₂O₃S₂ (20% in water) and dilute with water (1 L). Concentrate the aqueous mixture under vacuum to 1 L volume. Add hexane and ethyl acetate 95/5 (500 mL), and stir vigorously for 20 min. Filter; wash with water, then with hexane; and dry the resulting cake under vacuum to afford 3-(4-chlorophenyl)-4-methylisothiazol-5-ylamine. Yield: 64.1%. LCMS: 225.0 (m+1).

Preparation II-7, Q=4-Bromophenyl: 3-(4-bromophenyl)-4-methylisothiazol-5-yl-amine. ES-MS: m/e 257.0 (m+1).

Preparation of a Phenol of Formula III

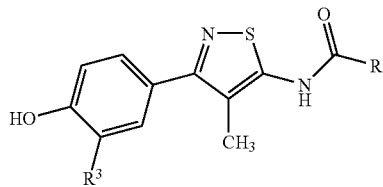

III

A phenol of formula III, in which R³ has the indicated value and R—CO is (R,R)-2-methylcyclopropanecarbonyl, is prepared using the corresponding compound of formula II in which R¹ is methyl and a similar procedure to that of Preparation III-1, below.

Preparation III-1, R³=H: (R,R)—N-[3-(4-Hydroxyphenyl)-4-methylisothiazol-5-yl]-2-methylcyclopropanecarboxamide.

A. 4-(5-Amino-4-methylisothiazol-3-yl)phenol.

Add boron tribromide (0.227 g, 0.909 mmol) to a solution of 3-(4-methoxy-phenyl)-4-methylisothiazol-5-ylamine (0.100 g, 0.455 mmol) in dichloromethane (5 mL) at −20° C. Stir and allow to warm to room temperature. Stir 4 h and quench with 1 N HCl. Extract with EtOAc (2 times 50 mL). Dry (MgSO₄) and evaporate. The product is used for the next step without further purification. Yield: 106.8% ES-MS: m/e 207.0 (m+1).

B. (R,R)—N-[3-(4-Hydroxyphenyl)-4-methylisothiazol-5-yl]-2-methylcyclopropane-carboxamide.

Add oxalyl chloride (2 M in dichloromethane, (0.291 mL, 0.583 mmol) to a stirred solution of (R,R)-2-methylcyclopropanecarboxylic acid (0.06 g, 0.58 mmol) and DMF (1 drop-catalytic) in toluene (1 mL). Stir 3 h and add the now formed acid chloride to a stirred solution of 4-(5-amino-4-methylisothiazol-3-yl)phenol (0.060 g, 0.291 mmol) and pyridine (0.07 g, 0.87 mmol) in THF (1 mL). Stir 1 h and dilute with EtOAc (300 mL), and wash with 1 N NaOH (2 times 100 mL)

then water (100 mL), dry (MgSO$_4$) and evaporate. Crystallize from chloroform and hexane. Yield: 64.6%. ES-MS: m/e 289.0 (m+1).

Preparation of a Nitrile of Formula IX

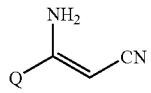

IX

Except as otherwise described, a nitrile of formula IX, having the indicated value of Q, is prepared using the corresponding benzonitrile of formula Q-CN and acetonitrile and a similar procedure to that of Preparation IX-2, below.

Preparation IX-2, Q=3-Fluoro-4-methoxyphenyl:

Combine 3-fluoro-4-methoxybenzonitrile (25.000 g, 165.563 mmol) and acetonitrile (13.576 g, 331.126 mmol) and THF (33 mL). Add potassium t-butoxide in THF (1 M, 182.1 mL, 182.1 mmol) with stirring. Stir overnight. Dilute with satd NaHCO$_3$ and extract with EtOAc. Evaporate the organic solution and crystallize from hexane/EtOAc to afford 3-amino-3-(3-fluoro-4-methoxyphenyl)acrylonitrile. Yield: 78.6%. ES-MS: m/e 193.0 (m+1).

Preparation IX-4, Q=Phenyl: 3-amino-3-phenylacrylonitrile.

Preparation IX-8, Q=3,4-Dichlorophenyl:

Using a similar procedure to that of Preparation IX-2, but using 1.5 equivalents of potassium t-butoxide and 1.5 equivalents of acetonitrile per 1 equivalent of 3,4-dichlorobenzonitrile, there is obtained 3-amino-3-(3,4-dichlorophenyl)acrylonitrile.

Preparation IX-9, Q=4-(Methylthio)phenyl:

Using a similar procedure to that of Preparation IX-2, but using 1.5 equivalents of potassium t-butoxide and 1.5 equivalents of acetonitrile per 1 equivalent of 4-(methylthio) benzonitrile, there is obtained 3-amino-3-[4-(methylthio)phenyl]acrylonitrile.

Preparation IX-10, Q=4-(1,1-Difluoroethyl)phenyl: 3-amino-3-[4-(1,1-difluoroethyl)-phenyl]acrylonitrile.

The starting 4-(1,1-difluoroethyl)benzonitrile for Preparation IX-10 is obtained as follows:

Add bis-(2-methoxyethyl)aminosulfur trifluoride (30.516 g, 137.931 mmol) to 4-acetylbenzonitrile (10.000 g, 68.966 mmol) and stir under a nitrogen atmosphere in a Teflon flask for 24 hr. Dilute with dichloromethane, followed by excess satd NaHCO$_3$ to quench. Extract with EtOAc, dry (MgSO$_4$) and evaporate. Chromatograph on silica gel, eluting with hexane and EtOAc (gradient of 3-30%), to afford 4-(1,1-difluoroethyl)-benzonitrile. Yield: 68.6%.

Preparation of a Thioamide of Formula X

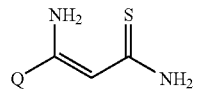

X

Except as otherwise described, a thioamide of formula X, having the indicated value of Q, is prepared using the corresponding nitrile of formula IX and a similar procedure to that of Preparation X-2, below.

Preparation X-2, Q=3-Fluoro-4-methoxyphenyl:

Add dioxane (65 mL) to 3-amino-3-(3-fluoro-4-methoxyphenyl)acrylonitrile (25.0 g, 130 mmol) and thioacetamide (19.5 g, 260 mmol); then add 4 N HCl in dioxane (650 mL, 2,600 mmol) and allow the reaction to stir 4-8 h until complete by TLC. Evaporate the reaction mixture to dryness; then add dioxane (200 mL); add slowly TEA (dried with K$_2$CO$_3$, 1000 mL); and then add satd K$_2$CO$_3$ (1000 mL) and extract with EtOAc (2000 mL). Dry the organic phase (K$_2$CO$_3$) and evaporate to afford 3-amino-3-(3-fluoro-4-methoxyphenyl)thioacrylamide. Yield: 98.5%. ES-MS: m/e 227.0 (m+1).

Preparation X-4, Q=Phenyl: 3-amino-3-(phenyl)-thioacrylamide.

Preparation X-8, Q=3,4-Dichlorophenyl: 3-amino-3-(3,4-dichlorophenyl)-thioacrylamide.

Preparation X-9, Q=4-(Methylthio)phenyl: 3-amino-3-[4-(methylthio)phenyl]-thioacrylamide.

Preparation X-10, Q=4-(1,1-Difluoroethyl)phenyl:

Add diphenylphosphinodithioic acid (13.2 g, 52.9 mmol) to a solution of 3-amino-3-[4-(1,1-difluoroethyl)phenyl] acrylonitrile (5.50 g, 26.4 mmol) in propan-2-ol (264 mL). Heat to 45° C. for 4 h. Dilute with EtOAc (400 mL), wash with brine 3× (100 mL), and evaporate. Crystallize from EtOAc/hexane to afford 3-amino-3-[4-(1,1-difluoroethyl)-phenyl] thioacrylamide. Yield: 67.2%. ES-MS: m/e 243.0 (m+1).

Preparation of an Amine of Formula VIII

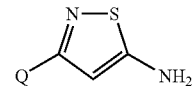

VIII

Except as otherwise described, an amine of formula VIII, having the indicated value of Q, is prepared using the corresponding thioamide of formula X and a similar procedure to that of Preparation VIII-2, below.

Preparation VIII-2, Q=3-Fluoro-4-methoxyphenyl:

Add hydrogen peroxide (30% in water, 8.73 g, 257 mmol) to 3-amino-3-(3-fluoro-4-methoxyphenyl)-thioacrylamide (29.0 g, 128 mmol) in methanol (1,283 mL) and stir the reaction mixture at room temperature. Quench the reaction with Na$_2$S$_2$O$_3$ (20% in water) and concentrate to dryness. Dilute with EtOAc (900 mL) and water (900 mL), collect the organic phase, and evaporate. Crystallize from EtOAc/hexanes to afford 3-(3-fluoro-4-methoxyphenyl)isothiazol-5-ylamine (1 g). Chromatography of the mother liquor (25 g) over silica gel, eluting with 25-50% EtOAc in hexane, affords additional product. [In one instance, a column loading accident led to loss of ½ of the material; but additional clean material was recovered from the chromatography (1 g).] Yield: 12.2%. ES-MS: m/e 225.0 (m+1).

Preparation VIII-4, Q=Phenyl: 3-phenylisothiazol-5-ylamine. ES-MS: m/e 177.2 (m+1).

Preparation VIII-8, Q=3,4-Dichlorophenyl: 3-(3,4-dichlorophenyl)isothiazol-5-yl-amine. ES-MS: m/e 247.0 (m+1).

Preparation VIII-9, Q=4-(Methylthio)phenyl: 3-[4-(methylthio)phenyl]isothiazol-5-yl-amine. ES-MS: m/e 222.3 (m+1).

Preparation VIII-10, Q=4-(1,1-Difluoroethyl)phenyl: 3-[4-(1,1-difluoroethyl)phenyl]-isothiazol-5-ylamine. ES-MS: m/e 241.2 (m+1).

Preparation of an Isothiazole of Formula VII

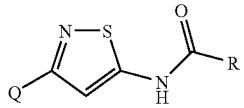

VII

Except as otherwise described, an amide of formula VII, having the indicated value of Q, is prepared using the corresponding amine of formula VIII and a similar procedure to that of Preparation VII-2, below.

Preparation VII-1, Q=4-Methoxyphenyl:
Using the Benzyl Ester and Trimethylaluminum:

To a stirred suspension of 3-(4-methoxyphenyl)isothiazol-5-ylamine (5.0 g, 24.3 mmol) in anhydrous dichloromethane (230 mL), cooled to 0-5° C., is added trimethylaluminum (2.0 M in toluene, 12.1 mL, 24.2 mmol) by syringe. The solution is stirred 5 min, and benzyl (R,R)-2-methylcyclopropanecarboxylate (4.6 g, 24.21 mmol) is added with the aid of anhydrous dichloromethane (10 mL). The mixture is then warmed to 40-45° C. with $N_2$ flow (needle bleed valve) to slowly remove solvent. After 2 h, most of the dichloromethane has been removed, and the internal temperature rises to about 50° C. The solution is stirred further for 3 h, cooled, and quenched cautiously with dropwise addition of water followed by 0.1 N HCl under a good $N_2$ stream. The resulting residue is then partitioned between ethyl acetate (400 mL) and 0.1 N HCl (400 mL). The organic layer is dried over potassium carbonate, filtered, and evaporated to a low volume. The resulting suspension is diluted with hexanes and the solid filtered to afford 5.9 g of crude product which is re-suspended in MTBE (100 mL), warmed to mild reflux for 1 h, and cooled to room temperature. After standing 1 h, the solid was filtered and dried (20 mm Hg, 40° C.) to afford (R,R)—N-[3-(4-methoxyphenyl)isothiazol-5-yl]-2-methyl-cyclopropanecarboxamide (5.2 g, 75%). $^1$H NMR (DMSO-$d_6$) δ7.86 (d, J=8.8 Hz, 2H), 7.20 (s, 1H), 7.00 (d, J=8.8 Hz, 2H), 3.78 (s, 3H), 1.62 (m, 1H), 1.34 (m, 1H), 1.10 (d, J=6.0 Hz, 3H), 1.09 (m, 1H), 0.80 (m, 1H); ES-MS m/e 289 (m+H).

Preparation VII-2, Q=3-Fluoro-4-methoxyphenyl:
Using the Benzyl Ester and Trimethylaluminum:

Add benzyl (R,R)-2-methylcyclopropanecarboxylate (0.55 g, 2.89 mmol) to a 0° C. solution of 3-(3-fluoro-4-methoxyphenyl)isothiazol-5-ylamine (0.59 g, 2.63 mmol) and trimethylaluminum (2.0 M in toluene, 5.26 mmol) in dichloromethane (5 mL) and allow reaction to naturally warm to room temperature. Warm the reaction mixture to 40° C. and allow to stir overnight. Dilute the reaction mixture with EtOAc (100 mL) and 1 N HCl (40 mL) and water (100 mL), collect the organic phase, and evaporate. Chromatography over silica gel eluting with 25-50% EtOAc in hexane affords (R,R)—N-[3-(3-fluoro-4-methoxyphenyl)isothiazol-5-yl]-2-methylcyclopropane-carboxamide. Yield: 55.9%. ES-MS: m/e 307.0 (m+1).

Preparation VII-4, Q=Phenyl: (R,R)-2-methyl-N-(3-phenyl-isothiazol-5-yl)-cyclopropanecarboxamide. ES-MS: m/e 259.2 (m+1).

Preparation VII-8, Q=3,4-Dichlorophenyl: (R,R)—N-[3-(3,4-dichlorophenyl)isothiazol-5-yl]-2-methylcyclopropanecarboxamide. ES-MS: m/e 328.0 (m+1).

Preparation VII-9, Q=4-(Methylthio)phenyl: (R,R)—N-[3-[4-(methylthio)phenyl]-isothiazol-5-yl]-2-methylcyclopropanecarboxamide. ES-MS: m/e 305.2 (m+1).

Preparation VII-10, Q=4-(1,1-Difluoroethyl)phenyl:
Using the Benzyl Ester and Potassium t-Butoxide:

Mix 3-[4-(1,1-difluoroethyl)phenyl]isothiazol-5-ylamine (0.200 g, 0.833 mmol), benzyl (R,R)-2-methylcyclopropanecarboxylate (0.238 g, 1.250 mmol) and potassium t-butoxide (0.190 g, 1.667 mmol) for 1 h. Dilute with satd NaHCO$_3$ and extract with EtOAc. Wash the organic phase with brine, dry (MgSO$_4$) and evaporate. Chromatography on silica gel, eluting with 10% EtOAc in CHCl$_3$, affords (R,R)—N-[3-[4-(1,1-difluoroethyl)phenyl]isothiazol-5-yl]-2-methylcyclopropane-carboxamide. Yield: 50.3%. ES-MS: m/e 323.3 (m+1).

Preparation of a 4-Bromoisothiazole of Formula VI, X = Br

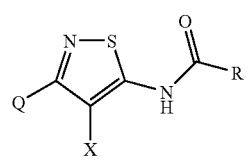

VI

Except as otherwise described, an amide of formula VI, in which X is bromo, having the indicated value of Q, is prepared using the corresponding amide of formula VII and a similar procedure to that of Preparation VI-2, below.

Preparation VI-2, Q=3-Fluoro-4-methoxyphenyl:
Add bromine (0.15 mL, 0.47 g, 2.94 mmol) to (R,R)—N-[3-(3-fluoro-4-methoxy-phenyl)isothiazol-5-yl]-2-methyl-cyclopropanecarboxamide (0.45 g, 1.47 mmol) in dichloromethane (3 mL) dropwise. Monitor by TLC and stop bromine addition when complete. Dilute the reaction mixture with EtOAc (100 mL) and pour into aqueous Na$_2$S$_2$O$_3$ (1 N). Collect the organic phase, wash with brine (50 mL) and water (80 mL), and evaporate. Chromatograph over silica gel, eluting with 10-50% EtOAc in hexane, to afford (R,R)—N-[4-bromo-3-(3-fluoro-4-methoxyphenyl)isothiazol-5-yl]-2-methyl-cyclopropanecarboxamide. Yield: 97.1%. ES-MS: m/e 387.0 (m+1).

Preparation VI-4, Q=Phenyl: (R,R)—N-[4-bromo-3-phenyl-isothiazol-5-yl]-2-methyl-cyclopropanecarboxamide. ES-MS: m/e 339.1 (m+1).

Preparation VI-8, Q=3,4-Dichlorophenyl: (R,R)—N-[4-bromo-3-(3,4-dichlorophenyl)-isothiazol-5-yl]-2-methylcyclopropanecarboxamide. ES-MS: m/e 406.8 (m+1).

Preparation VI-9, Q=4-(Methylthio)phenyl: (R,R)—N-[4-bromo-3-[4-(methylthio)-phenyl]isothiazol-5-yl]-2-methylcyclopropanecarboxamide. ES-MS: m/e 385.0 (m+1).

Preparation VI-10, Q=4-(1,1-Difluoroethyl)phenyl: (R,R)—N-[4-bromo-3-[4-(1,1-difluoroethyl)phenyl]isothiazol-5-yl]-2-methylcyclopropanecarboxamide. ES-MS: m/e 403.0 (m+1).

Preparation of 3,4-Dibromoisothiazole of Formula XI

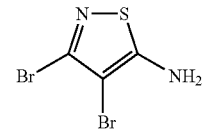

XI

To a stirring solution of 2-cyanothioacetamide (39.5 g, 0.395 mol) in dichloro-methane (700 mL) at 0° C. is added glacial acetic acid (79 mL). Then, a solution of bromine (43.0 mL, 0.840 mol) in dichloromethane (395 mL) is added dropwise over 2 h while keeping the temperature at 0° C. The mixture is stirred 1 h longer in the cold, and then quenched by addition to 10% aqueous sodium bisulfite (300 mL). The aqueous layer is treated with 2 N aqueous sodium carbonate until the pH is 9, brought to room temperature, and the biphasic mixture filtered through diatomaceous earth, which is washed with dichloromethane. After the layers are separated, the dark organic layer is dried ($Na_2SO_4$) and evaporated to a dark solid, which is re-dissolved in dichloromethane, added as such to a silica gel column, then chromatographed, eluting with 20% ethyl acetate in hexanes, to afford 3,4-dibromoisothiazol-5-ylamine as an off-white solid (12 g, 12%). ES-MS m/E 259 (m+1).

Preparation of 3,4-Dibromoisothiazole of Formula XII

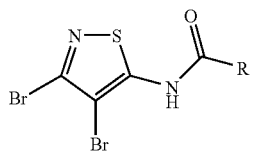

XII

To (R,R)-2-methylcyclopropanecarboxylic acid (5.4 g, 36 mmol) in dichloromethane (100 mL) is added DMF (two drops), followed by 98% oxalyl chloride (4.8 mL, 54 mmol). The mixture is stirred 3 h at room temperature.

In a separate flask is dissolved 3,4-dibromoisothiazol-5-ylamine (9.3 g, 36.05 mmol), in THF (200 mL) and, after cooling the THF solution to 0° C., triethylamine (30 mL, 215 mmol). The above formed acid chloride solution is added dropwise at 0° C., the mixture is brought to room temperature, and stirred overnight (16 h). The dark solution is partitioned with brine (800 mL) and ethyl acetate (800 mL). The organic layer is dried ($Na_2SO_4$) and evaporated to a dark oil. Chromatography over silica gel (flash 65, 10% ethyl acetate in toluene) affords the crude product as a solid, which is recrystallized from dichloromethane/hexanes to provide (R,R)—N-[3,4-dibromo-isothiazol-5-yl]-2-methylcyclopropanecarboxamide (4.0 g, 33%):

$^1$H NMR (DMSO-$d_6$) δ 11.90 (s, 1H), 2.09 (m, 1H), 1.40 (m, 1H), 1.12 (m, 1H), 1.11 (d, J=6.0 Hz, 3H), 0.85 (m, 1H); ES-MS m/e 339 (m−H).

Alternative Preparation of a 4-Bromoisothiazole of Formula VI, X = Br

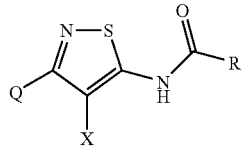

VI

Except as otherwise described, an amide of formula VI, in which X is bromo, having the indicated value of Q, is prepared using the corresponding a boronic acid Q-B(OH)$_2$ and an amide of formula XII, (R,R)—N-[3,4-dibromoisothiazol-5-yl]-2-methyl-cyclopropanecarboxamide, and a similar procedure to that of Alternative Preparation VI-3, below.

Alternative Preparation VI-3, Q=4-Ethoxyphenyl:

Degas a solution of (R,R)—N-[3,4-dibromoisothiazol-5-yl]-2-methylcyclopropane-carboxamide (0.500 g, 1.471 mmol), (4-ethoxyphenyl)boronic acid (0.485 g, 2.941 mmol), DMF (3 mL) and toluene (29 mL) with nitrogen. Add sodium carbonate (2 M) (4.41 mmol) and Pd(PPh$_3$)$_4$ (0.255 g, 0.221 mmol); then seal under nitrogen. Heat at 60° C. overnight. Add 100 mg of Pd(PPh$_3$)$_4$ and heat for 1 more day. Dilute with EtOAc and wash with brine. Separate and evaporate. Chromatography on silica gel, eluting with 15-50% EtOAc in hexane, followed by crystallization from EtOAc and hexane affords (R,R)—N-[4-bromo-3-(4-ethoxyphenyl)isothiazol-5-yl]-2-methylcyclopropane-carboxamide. Yield: 53.5% ES-MS: 380.0 (m+1).

Alternative Preparation VI-5, Q=4-Fluorophenyl:

Using a similar procedure to that of Preparation VI-3, but using 1.3 equivalents of 4-fluorophenylboronic acid to 1 equivalent of (R,R)—N-[3,4-dibromoisothiazol-5-yl]-2-methylcyclopropanecarboxamide and stirring the reaction mixture at 70° C. for 1 day affords (R,R)—N-[4-bromo-3-(4-fluorophenyl)isothiazol-5-yl]-2-methylcyclopropane-carboxamide. ES-MS: m/e 357.0 (m+1).

EXAMPLES OF FORMULA I

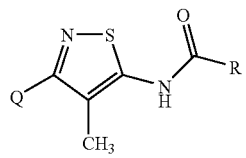

I

Except as otherwise described, an amide of formula I, having the indicated value of Q, is prepared using the corresponding amine of formula II and a similar procedure to that of Example 1, below.

Example 1

Q=4-Methoxyphenyl, Using Procedure (A)

Using the Benzyl Ester and Trimethylaluminum:

Add trimethylaluminum (2 M in toluene, 3.59 g, 45.5 mmol) to a 0° C. solution of 3-(4-methoxyphenyl)-4-methyl-isothiazol-5-ylamine (10.0 g, 45.5 mmol) in dichloromethane (455 mL). Stir 5 min and add benzyl (R,R)-2-methylcyclopropane-carboxylate (8.64 g, 45.5 mmol). Heat to 50° C. with nitrogen flow to remove solvent. The resulting oil is heated at 50° C. for 3 h. Quench with water and dilute with EtOAc (300 mL). Wash with 0.1 N HCl, dry (K$_2$CO$_3$), evaporate, and crystallize from hexane/EtOAc to afford (R,R)—N-[3-(4-methoxyphenyl)-4-methylisothiazol-5-yl]-2-methylcyclo-propanecarboxamide. Yield: 80.4%. ES-MS: m/e 303.0 (m+1). (The mother liquor may be used for further recrystallizations.)

Using the Acid Chloride:

Oxalyl chloride (170 g, 120 mL, 1.05 equivalent) is added dropwise over about 1.5 h to a solution at 21° C. of (R,R)-2-methylcyclopropanecarboxylic acid (150 g, 1.06 equivalent) and DMF (catalytic, 0.03 equivalent) in dichloromethane (1.30 L), during which time the endothermic reaction cools the mixture to about 16° C. The reaction mixture is stirred at ambient temperature 30 min; then it is heated to reflux for 30 min to afford a solution of (R,R)-2-methylcyclopropanecarbonyl chloride, which is cooled to 25° C. for use in the next step.

To a solution of 3-(4-methoxyphenyl)-4-methylisothiazol-5-ylamine (280 g, 1.00 equivalent) and pyridine (catalytic, 0.03 equivalent) in anhydrous THF (350 mL) is added the above acid chloride solution dropwise over 30 min at 6 to 13° C.; and the reaction mixture is stirred at room temperature 1 h. (The progress of the reaction may be followed by HPLC, and acid chloride addition terminated if monitoring indicates complete reaction of the amine.) Water (2.5 L) is added, the phases are separated and aqueous phase is re-extracted with dichloromethane. The combined organic phase is washed (aqueous NaOH (1 L), then water (1 L)). partially evaporated to about 1 kg, and then diluted with THF (2 L) to give an homogeneous solution, from which some water separates. The mixture is allowed to stand overnight at room temperature during which the two phases separate, with the aqueous phase above the organic phase. The phases are separated, THF is added to each phase, water is added to the upper (organic) phase, and each layer is reequilibrated, with very slow phase separation and the organic phase as the top layer. The combined organic phase is charged to a rotary evaporator (10-L flask) through a clarifying membrane (5 μm), toluene (4 L) is added, resulting in opacification of the mixture, and THF/water are evaporated (160 mbar, bath temp 45° C.). As the THF/water are evaporated, crystals begin to form. When 2 L has been distilled, toluene (2 L) is added and distillation continued (85 mbar, bath temp 45° C.). After distillation of a further 2 L of solvent, the system is set to atmospheric pressure, cooled to ambient temperature, and, after 1 h, the resulting suspension is filtered. The filter cake is resuspended in toluene (1 L), refiltered, and washed with toluene (1 L) before it is dried overnight to afford (R,R)—N-[3-(4-methoxyphenyl)-4-methylisothiazol-5-yl]-2-methylcyclopropanecarboxamide. Yield: 357 g, 92%.

For monitoring the reaction by HPLC: column: XTerra MS C18 2.5 μm; 4.6×50 mm; eluent A, 0.1% TFA in water; eluent B, acetonitrile; flow rate 1.50 mL/min; approximate gradient A/B: 0-0.5 min at 85/15, 1.5 to 7 min 85/15 to 5/95, 7 min to 7.5 min at 5/95, 7.5-8 min 5/95 to 85/15, 8-10 min at 85/15; run time, 10 min; detection, UV, 210 nm; sample preparation, diluted in 70:30:1 acetonitrile-water-TFA.

The enantiomeric excess (ee) and stereochemical purity of the carboxamide may be determined by HPLC: stationary phase (column): Chiralcel OJ (240×4.6 mm, i.d.) from Daicel column; mobile phase: methanol:diethyl amine (100:0.1 v/v); detection: UV at 280 nm; injection volume: 5 μL; sample temp: 20° C.; column temp: ambient; run time: 20 min; sample solvent: methanol; sample concentration: about 5 mg/mL methanol. In a typical chromatogram (R,R)—N-[3-(4-methoxyphenyl)-4-methylisothiazol-5-yl]-2-methyl-cyclopropanecarboxamide has a retention time of 10.519 min, the (S,S)-isomer has a retention time of 12.981 min, and the trace amounts of the two cis-2-methyl isomers have retention times of 14.189 min and 14.980 min. The ee and percent of cis-impurities of a typical preparation will depend upon the ee and percent of cis-impurities of the starting acid and the degree of further purification by (re)crystallization. Typical preparations as described above provide an ee of greater than 97% and cis-impurities of about 0.5% to about 1%.

In general, the compound of Example 1, when prepared and isolated as described in the examples herein is obtained as a crystalline solid as determined by microscopy, X-ray powder diffraction (XRPD) and/or differential scanning calorimetry (DSC). The preparations which have been examined by XRPD are characterized by absorptions at (°2θ, relative intensity): 5.944, 1.00; 13.856, 0.01; 15.445, 0.01; 17.806, 0.06; 19.797, 0.02; 22.718, 0.02; 23.812, 0.01; and, more particularly, by absorptions at (°2θ, relative intensity): 5.944, 1.00; 17.806, 0.06; 19.797, 0.02; 22.718, 0.02; and denoted as Anhydrous Form I. When the compound is slurried in methanol/water mixtures, a second form denoted as Anhydrous Form II, characterized by absorptions at (°2θ, relative intensity): 6.727, 1.00; 11.371, 0.04; 18.159, 0.04; 20.220, 0.12; 22.782, 0.09; 30.026, 0.04; 36.818, 0.02; 25.482; 0.03; and, more particularly, by absorptions at (°2θ, relative intensity): 6.727, 1.00; 20.220, 0.12; 22.782, 0.09, is obtained under conditions of lower water activity ($a_W$), for example at $a_W$ less than or equal to 0.66; and a monohydrated form denoted as Monohydrate I, characterized by absorptions at (°2θ, relative intensity): 5.193, 0.07; 10.336, 0.82; 14.005, 0.77; 20.686, 0.19; 22.907, 1.00; 24.716, 0.53; 26.375, 0.29; and, more particularly by absorptions at (°2θ, relative intensity): 10.336, 0.82; 14.005, 0.77; 22.907, 1.00; 24.716, 0.53, is obtained under conditions of higher water activity, for example at $a_W$ greater than or equal to 0.91.

XRPD patterns were obtained on a Bruker D8 Advance X-ray powder diffractometer, equipped with a CuKα source (λ=1.54056 Å) and an electronic Sol-X detector, operating at minimally 30 kV and 40 mA. Each sample was scanned at room temperature (25° C.) between 4° and 40° in 2θ, with a step size of 0.02° in 2θ and a maximum scan rate of 3 sec/step, and with controlled variable (v 12) divergence and receiving slits and a 0.1 mm detector slit.

Example 1

Q=4-Methoxyphenyl, Using Procedure (B)

To a dry flask containing (R,R)—N-[3-(4-hydroxyphenyl)-4-methylisothiazol-5-yl]-2-methylcyclopropanecarboxamide (100 mg, 0.347 mmol) is added dry acetone (2 mL), $K_2CO_3$ (50 mg, 0.347 mmol), and methyl iodide (19 μL, 0.313 mmol). The reaction mixture is heated 16 h at 45° C. and treated with additional methyl iodide (19 μL, 0.313 mmol). After heating for another 6 h, the solvent is evaporated, and the residue is partitioned between ethyl acetate and water. The ethyl acetate solution is washed (satd aqueous $K_2CO_3$ (twice) and brine), dried ($MgSO_4$), and the solvent evaporated. Chromatography over silica gel, eluting with EtOAc/hexanes, affords (R,R)—N-[3-(4-methoxyphenyl)-4-methylisothiazol-5-yl]-2-methylcyclopropane-carboxamide (35 mg, 33%) as a white solid. $^1$H NMR; ES-MS: m/e 303 (m+1).

Example 2

Q=3-Fluoro-4-Methoxyphenyl, Using Procedure (C)—Coupling with a Compound of Formula VI, X=Br Add $PdCl_2(PPh_3)_2$ (0.15 g, 0.21 mmol) and $Sn(CH_3)_4$ (0.79 mL, 1.02 g, 5.71 mmol) to (R,R)—N-[4-bromo-3-(3-fluoro-4-methoxyphenyl)-isothiazol-5-yl]-2-methylcyclopropanecarboxamide (0.55 g, 1.43 mmol) in DMF (3 mL), and stir the reaction mixture at 130° C. in a sealed tube overnight. Dilute with EtOAc (100 mL) and brine (100 mL). Collect the organic phase, dry ($K_2CO_3$) and evaporate. Take up the resultant oil in 1:1 MTBE:KF (aqueous, 15%) (50 mL) and stir at reflux for 1 h. Pour the cooled solution over diatomaceous earth and filter with MTBE (100 mL). Collect the organic phase, dry ($K_2CO_3$) and evaporate. Chromatography over silica gel, eluting with 10-30% THF in hexane, affords (R,R)—N-[3-(3-fluoro-4-methoxyphenyl)-4-methylisothiazol-5-yl]-2-methylcyclopropanecarboxamide. Yield: 49.2%. ES-MS: m/e 321.0 (m+1).

Example 3

Q=4-Ethoxyphenyl, Using Procedure (C)—Coupling with a Compound of Formula VI, X=Br Add $PdCl_2(PPh_3)_2$ (0.07 g, 0.09 mmol) and $Sn(CH_3)_4$ (0.34 mL, 0.44 g, 2.48 mmol) to (R,R)—N-[4-bromo-3-(4-ethoxyphenyl)isothiazol-5-yl]-2-methylcyclopropane-carboxamide (0.24 g, 0.62 mmol) in DMF (1 mL) and stir the reaction mixture at 130° C. in a sealed tube overnight. Dilute with EtOAc (100 mL) and brine (100 mL). Collect the organic phase, dry (MgSO$_4$), and evaporate. Filter over silica gel and wash with EtOAc. Evaporate and crystallize from EtOAc/hexane to afford (R,R)—N-[3-(4-ethoxyphenyl)-4-methylisothiazol-5-yl]-2-methylcyclopropanecarboxamide. Yield: 81.7%.

ES-MS: m/e 317.0 (m+1).

Example 4

Q=Phenyl, Using Procedure (C)—Metalation-Methylation with a Compound of Formula VI, X=Br To (R,R)—N-[4-bromo-3-phenylisothiazol-5-yl]-2-methylcyclopropane-carboxamide (0.50 g, 1.48 mmol) in THF (3 mL), cooled to −78° C., is added 1.1 equivalent n-butyllithium (n-BuLi) (1.6M in hexane, 0.204 mL, 3.26 mmol). Internal temperature is maintained below −68° C. Following addition, the reaction mixture is allowed to stir for 1 h. 1.1 additional equivalents of n-BuLi (1.6M in hexane, 0.204 mL, 3.26 mmol) is then added while keeping the internal temperature below −66° C. After stirring for 2 h, the reaction mixture is warmed to −40° C. for 15 min; and then cooled back down to −78° C. Methyl iodide (0.10 mL, 1.63 mmol) is then added. The reaction mixture is allowed to warm to room temperature and stir over a weekend before the reaction is quenched with satd NH$_4$Cl and diluted with EtOAc. The organic phase is washed with brine, dried (K$_2$CO$_3$) and evaporated. Chromatography over silica gel, eluting with 5-35% EtOAc in hexane, affords (R,R)-2-methyl-N-(4-methyl-3-phenylisothiazol-5-yl)-cyclopropanecarboxamide. Yield: 16.4%. ES-MS: 273.2 (m+1).

Example 5

Q=4-Fluorophenyl, Using Procedure (C)—Coupling with a Compound of Formula VI, X=Br A similar procedure to that of Example 3, using (R,R)—N-[4-bromo-3-(4-fluorophenyl)isothiazol-5-yl]-2-methylcyclopropanecarboxamide, affords (R,R)—N-[3-(4-fluorophenyl)-4-methylisothiazol-5-yl]-2-methylcyclopropanecarboxamide. ES-MS: m/e 291.0 (m+1).

Example 6

Q=4-Chlorophenyl, Using Procedure (A): (R,R)—N-[3-(4-chlorophenyl)-4-methylisothiazol-5-yl]-2-methylcyclopropanecarboxamide ES-MS: m/e 307.0 (m+1).
Using the Acid Chloride:
To a solution of (R,R)-2-methylcyclopropanecarboxylic acid (7 65 mL, 7.83 g, 1.00 equiv) in dichloromethane (HPLC grade, 39.2 mL, 5 mL/g of acid), add dimethyl-formamide (30 μL, 390 μmol, 0.005 mol/mol acid), followed by the slow addition of oxalyl chloride (6.85 mL, 77.4 mmol, 0.99 mol/mol acid) at 0° C. (ice-water bath) under a nitrogen atmosphere. Remove the ice bath after 30 min, and warm to 40° C. for 30 min. Allow the solution to cool to ambient temperature and directly use in the next step without any other treatment.
To a solution of 3-(4-chlorophenyl)-4-methylisothiazol-5-ylamine (17.1 g, 75.9 mmol, 1 equiv), pyridine (12.3 mL, 152 mmol, 2 moles/mol amine), and dichloromethane (75.9 mL to give a 1 M of the amine) in a 500 mL round bottom flask (fitted with nitrogen blanket, stir bar and cooling bath), add the above preformed solution of (R,R)-2-methylcyclopropanecarbonyl chloride (1.00 equiv; 75.9 mmol). Stir 30 min; then remove the ice bath and stir 3 h. Concentrate the reaction mixture under vacuum and dilute with ethyl acetate. Wash 2 times with dilute HCl and 2 times with aqueous NaHCO$_3$, dry (K$_2$CO$_3$), filter, and evaporate to dryness. Crystallize from hexane and ethyl acetate to yield a white solid, and collect a second crop by repeating the crystallization to afford (R,R)—N-[3-(4-chlorophenyl)-4-methylisothiazol-5-yl]-2-methylcyclopropanecarboxamide. Yield: 92.2%. LCMS: 307.0 (m+1). $^1$H NMR (DMSO-d$_6$, 300 MHz) δ 11.26 (s, 1H), 7.62 (d, 2H, J=8.8 Hz), 7.50 (d, 2H, J=8.8 Hz), 2.28 (s, 3H), 1.90 (m, 1H), 1.32 (m, 1H), 1.11 (m, 4H), 0.79 (m, 1H).

Example 7

Q=4-Bromophenyl, using procedure (A): (R,R)—N-[3-(4-bromophenyl)-4-methylisothiazol-5-yl]-2-methylcyclopropanecarboxamide ES-MS: m/e 353.0 (m+1).

Example 8

Q=3,4-Dichlorophenyl, Using Procedure (C)—Coupling with a Compound of Formula VI, X=Br A similar procedure to that of Example 2, using (R,R)—N-[4-bromo-3-(3,4-dichlorophenyl)isothiazol-5-yl]-2-methylcyclopropanecarboxamide, affords (R,R)—N-[3-(3,4-dichlorophenyl)-4-methylisothiazol-5-yl]-2-methylcyclopropane-carboxamide. ES-MS: m/e 341.0 (m+1).

Example 9

Q=4-(Methylthio)phenyl, Using Procedure (C)—Coupling with a Compound of Formula VI, X=Br A similar procedure to that of Example 2, using (R,R)—N-[4-bromo-3-[4-(methylthio)phenyl]isothiazol-5-yl]-2-methylcyclopropanecarboxamide, affords (R,R)—N-[3-[4-(methylthio)phenyl]-4-methylisothiazol-5-yl]-2-methylcyclopropane-carboxamide. ES-MS: m/e 319 (m+1).

Example 10

Q=4-(1,1-Difluoroethyl)phenyl, Using Procedure (C)—Coupling with a Compound of Formula VI, X=Br A similar procedure to that of Example 2, using (R,R)—N-[4-bromo-3-[4-(1,1-difluoroethyl)phenyl]isothiazol-5-yl]-2-methylcyclopropanecarboxamide, affords (R,R)—N-[3-[4-(1,1-difluoroethyl)phenyl]-4-methylisothiazol-5-yl]-2-methyl-cyclopropanecarboxamide. ES-MS: m/e 337.3 (m+1).

What is claimed is:

1. A compound of formula I,

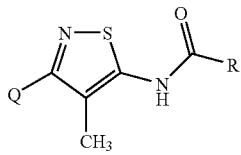

I or a pharmaceutically acceptable salt thereof, wherein

Q is a phenyl group of formula $Q^A$

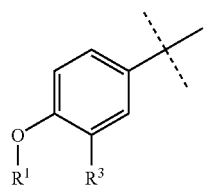

in which $R^1$ is methyl or ethyl, and $R^3$ is hydrogen or fluoro; or

Q is a phenyl group of formula $Q^B$

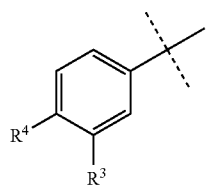

in which $R^3$ is hydrogen or fluoro and $R^4$ is hydrogen, fluoro, chloro or bromo; or each of $R^3$ and $R^4$ is chloro; or $R^3$ is hydrogen and $R^4$ is methylthio or 1,1-difluoroethyl; and R—CO is (R,R)-trans-2-methylcyclopropanecarbonyl.

2. The compound or salt of claim 1 wherein Q is 4-methoxyphenyl, 3-fluoro-4-methoxyphenyl, 4-ethoxyphenyl, phenyl, 4-fluorophenyl, 4-chlorophenyl, 4-bromophenyl, 3,4-dichlorophenyl, 4-(methylthio)phenyl or 4-(1,1-difluoroethyl)phenyl.

3. The compound or salt of claim 1 wherein Q is $Q^A$.

4. The compound or salt of claim 1 wherein Q is $Q^B$.

5. The compound or salt of claim 4 wherein $R^4$ is chloro.

6. The compound or salt of any one of claims 1 and 3-4 wherein $R^3$ is hydrogen.

7. The compound of claim 1 which is (R,R)—N-[3-(4-chlorophenyl)-4-methylisothiazol-5-yl]-2-methylcyclopropanecarboxamide, or a pharmaceutically acceptable salt thereof.

8. A pharmaceutical composition comprising a compound of formula I, or a pharmaceutically acceptable salt thereof, as claimed in claim 1 or claim 7 together with a pharmaceutically acceptable diluent, excipient or carrier.

9. A method of treating pain in a mammal in need of treatment comprising administering to the mammal an effective amount of a compound of formula I, or a pharmaceutically acceptable salt thereof, as claimed in claim 1 or claim 7.

10. The method of claim 9 wherein the pain is chronic pain.

* * * * *

UNITED STATES PATENT AND TRADEMARK OFFICE
CERTIFICATE OF CORRECTION

| | | |
|---|---|---|
| PATENT NO. | : 7,960,419 B2 | Page 1 of 1 |
| APPLICATION NO. | : 12/300415 | |
| DATED | : June 14, 2011 | |
| INVENTOR(S) | : Ryan Thomas Backer et al. | |

It is certified that error appears in the above-identified patent and that said Letters Patent is hereby corrected as shown below:

On Title Page Col. 1, item (75); Delete "Minniapolis," and insert --Minneapolis,--.

On Column 28, line 2, In Claim 1, delete "fluoro" and insert --fluoro,--.

Signed and Sealed this
Twenty-sixth Day of July, 2011

David J. Kappos
*Director of the United States Patent and Trademark Office*